United States Patent
Solis Herrera

(10) Patent No.: US 10,375,936 B2
(45) Date of Patent: Aug. 13, 2019

(54) ANIMAL MODELS OF CORNEAL ANGIOGENESIS AND CORNEAL ECTATIC DISEASES, METHODS OF PRODUCING, AND METHODS OF USE THEREOF

(71) Applicant: Arturo Solis Herrera, Aguascalientes (MX)

(72) Inventor: Arturo Solis Herrera, Aguascalientes (MX)

( * ) Notice: Subject to any disclaimer, the term of this patent is extended or adjusted under 35 U.S.C. 154(b) by 0 days.

(21) Appl. No.: 15/314,647

(22) PCT Filed: Jun. 3, 2015

(86) PCT No.: PCT/IB2015/000822
§ 371 (c)(1),
(2) Date: Nov. 29, 2016

(87) PCT Pub. No.: WO2015/185977
PCT Pub. Date: Dec. 10, 2015

(65) Prior Publication Data
US 2017/0196207 A1 Jul. 13, 2017

Related U.S. Application Data

(60) Provisional application No. 62/007,140, filed on Jun. 3, 2014.

(51) Int. Cl.
| | |
|---|---|
| *A61K 49/10* | (2006.01) |
| *A01K 67/027* | (2006.01) |
| *A61K 31/03* | (2006.01) |
| *A61K 31/05* | (2006.01) |
| *A61K 49/00* | (2006.01) |

(52) U.S. Cl.
CPC ............ *A01K 67/027* (2013.01); *A61K 31/03* (2013.01); *A61K 31/05* (2013.01); *A61K 49/0008* (2013.01); *A01K 2227/10* (2013.01); *A01K 2267/035* (2013.01)

(58) Field of Classification Search
None
See application file for complete search history.

(56) References Cited

U.S. PATENT DOCUMENTS

2005/0143463 A1* 6/2005 Krishnan ............... A61K 31/20
514/558
2008/0027021 A1 1/2008 Klinman et al.
2011/0076266 A1 3/2011 Gallo Barraco

FOREIGN PATENT DOCUMENTS

RU 2257911 C2 8/2005

OTHER PUBLICATIONS

Liu et al., In vivo corneal neovascularization imaging by opticalresolution photoacoustic microscopy. Photoacoustics 2 (2014) 81-86. (Year: 2014).*
Agency for Toxic Substances & Disease Registry (ATSDR), Medical Management Guidelines for Xylene, Oct. 21, 2014, pp. 1-20 (Year: 2014).*
Rowe et al. Handbook of Pharmaceutical Excipients, 5th ed. Pharma Press, London, 2006, pp. 514-515. (Year: 2006).*
Sharma et al., Effects of hydroquinone on retinal and vascular cells in vitro. Indian Journal of Ophthalmology. 2012, 60:189-193. (Year: 2012).*
Int'l Search Report and Written Opinion dated Sep. 30, 2015 in Int'l Application No. PCT/IB2015/000822.
Wang et al., "Pharmacological Characteristics and Efficacy of a Novel Anti-Angiogenic Antibody FD006 in Corneal Neovascularization", BMC Biotechnology, vol. 14, No. 17 , pp. 1-9 (Feb. 2014).
Velpandian et al., "Evaluation of Pharmacological Activities and Assessment of Intraocular Penetration of an Ayurvedic Polyherbal Eye Drop (Itone) in Experimental Models", BMC Comp Altern. Med., vol. 13, No. 1, pp. 1-12 (Jan. 2013).
Takeuchi et al., "Effects of Trehalose on VEGF-Stimulated Angiogenesis and Myofibroblast Proliferation: Implications for Glaucoma Filtration Surgery", Invest. Ophthal. & Visual Science, vol. 52, No. 9, pp. 6987-6993 (Aug. 2011).
Int'l Preliminary Report dated Dec. 6, 2016 in Int'l Application No. PCT/IB2015/000822.
Extended European Search Report and Search Opinion dated Dec. 20, 2017 in EP Application No. 15802883.7.
Flickinger, "The Benzenediols: Catechol Resorcinol and Hydroquinone—A Review of the Industrial Toxicology and Current Industrial Exposure Limits", American Industrial Hygiene Association Journal, vol. 37, No. 10, pp. 596-606 (1976).
Wolf et al., "Toxicological Studies of Certain Alkylated Benzenes and Benzene; Experiments on Laboratory Animals", AMA Archives of Industrial Health, vol. 14, No. 4, pp. 387-398 (1956).
Paranthan et al., "A Robust Model for Simultaneously Inducing Corneal Neovascularzation and Retinal Gliosis in the Mouse Eye", Molecular Vision, vol. 17, pp. 1901-1908 (2011).
Montezuma et al., "Review of the Ocular Angiogenesis Animal Models", Seminars in Ophthalmology, vol. 24, No. 2, pp. 52-61 (2009).
Office Action dated Dec. 19, 2017 in JP Application No. 2016-570955.
Ueda, "Free Radicals and Corneal Neovascularization—Rabbit Corneal Neovascularization Model", Journ. of the Eye, vol. 15, No. 5, pp. 625-630 (May 1998) (see p. 2 of the English translation of the Office Action dated Dec. 19, 2017 in JP Application No. 2016-570955 for concise description of relevance).

(Continued)

*Primary Examiner* — Kevin K Hill
*Assistant Examiner* — Arthur S Leonard

(57) ABSTRACT

Methods of producing non-human animal models of corneal angiogenesis and corneal ectatic diseases, such as corneal keratoconus, by applying an aromatic compound to the eye of a non-human animal are described. Also described are non-human animal models of corneal angiogenesis and corneal ectatic diseases, and methods of using the non-human animal models to screen compounds that modulate corneal angiogenesis and corneal ectatic diseases.

20 Claims, 2 Drawing Sheets

(56) References Cited

OTHER PUBLICATIONS

Office Action dated Oct. 18, 2017 in CA Aplication No. 2,953,244.
Office Action dated Nov. 21, 2017 in KR Application No. 10-2016-7036701.
Office Action and Search Report dated Mar. 2, 2018 in RU Application No. 2016152182.
Office Action dated Oct. 8, 2018 in EP Application No. 15802883.7.
Office Action dated Oct. 8, 2018 in CN Application No. 201580029958.6.

* cited by examiner

ANIMAL MODELS OF CORNEAL ANGIOGENESIS AND CORNEAL ECTATIC DISEASES, METHODS OF PRODUCING, AND METHODS OF USE THEREOF

CROSS-REFERENCE TO RELATED APPLICATIONS

This application is a Section 371 of International Application No. PCT/IB2015/000822, filed Jun. 3, 2015, which was published in the English language on Dec. 10, 2015 under International Publication No. WO 2015/185977 A1, which claims priority under 35 U.S.C. § 119(e) to U.S. Provisional Patent Application No. 62/007,140, filed Jun. 3, 2014, and the disclosures of which are herein incorporated by reference.

FIELD OF THE INVENTION

The invention relates to non-human animal models of corneal diseases, and in particular animal models of corneal angiogenesis and corneal ectatic diseases, such as corneal keratoconus.

BACKGROUND OF THE INVENTION

Angiogenesis is the physiological process by which new blood vessels form from preexisting blood vessels. The concept of inhibiting angiogenesis as a therapeutic strategy, particularly for treating tumors and cancers, has been discussed for several decades, and is now widely considered to be a promising approach for the treatment of a range of pathologies and disease states in which vascular proliferation is a component. Anti-angiogenesis strategies have now been pursued not only as anti-cancer therapies, but also for the treatment of arthritis, retinopathies, heart disease, and circulatory problems. Accordingly, experimental animal models of angiogenesis are important for studying angiogenesis and the growth of blood vessels, evaluating the effects of different compounds on angiogenesis, and for screening compounds to identify compounds having anti-angiogenic or pro-angiogenic activity.

The cornea has been considered an ideal model of in vivo angiogenesis because it is avascular, and therefore any vascular development (i.e., development of new blood vessels) can usually be directly attributed to a substance or compound applied to the corneal area of the eye. Therefore, many animal models developed to study in vivo angiogenesis are models of corneal angiogenesis. These animal models are commonly produced by introducing a cornea pocket, or iris implant, into the eye of an animal.

In the cornea pocket model, an inducer of angiogenesis, such as tumor tissue, a cell suspension, or growth factor is placed into a pocket formed in the cornea, which induces the formation of new blood vessels. However, formation of the cornea pocket is often a difficult procedure, typically performed by lamellar dissection with a scalpel to create a space or "pocket" in the cornea, into which the inducer of angiogenesis is introduced. Due to the surgical nature of the procedure, complications often result from the procedure including problems related to the anesthetic agent used, perforation of the anterior chamber of the eye during dissection, inadequate preparation of the inducer of angiogenesis, and angiogenesis resulting from the surgical wound itself or sutures used to stitch the surgical wound. Moreover, inflammatory reactions can occur due to tissue manipulation and suturing, as well as in response to the inducer of angiogenesis inserted into the cornea pocket, which is often a foreign substance. Reactions to the insertion of foreign materials in the eye can also cause fibrosis, which is the formation of excess fibrous connective tissue in an organ or tissue. Fibrosis is usually the result of a reparative or reactive process.

Moreover, to the best of the inventor's knowledge, there are currently no animal models of corneal ectatic diseases, such as corneal keratoconus. Corneal ectasia is the progressive bulging of the cornea due to thinning or weakening of the cornea, accompanied by vision deterioration, vision impairment, or both. Corneal keratoconus is one of the more common corneal ectatic diseases, and is characterized by a structural distortion of the cornea from the typical rounded shape to a conical shape that protrudes, or bulges, outward from the corneal area of the eye. Animal models of corneal ectatic diseases would provide tools for studying these diseases in vivo.

BRIEF SUMMARY OF THE INVENTION

Accordingly, there exists a need for new animal models of in vivo angiogenesis that overcome some of the disadvantages associated with prior art models of angiogenesis. There is also a need for animal models of corneal ectatic diseases that could be used to study these diseases. The invention satisfies this need by providing animal models of corneal angiogenesis that overcome certain disadvantages associated with prior art animal models of in vivo angiogenesis. The invention also provides animal models of corneal ectatic diseases, such as corneal keratoconus.

In one general aspect, the invention relates to a method of producing a non-human animal model of corneal angiogenesis, the method comprising applying to a cornea of at least one eye of a non-human animal an effective amount of an aromatic compound of formula (I):

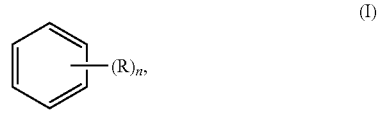

wherein R is selected from the group consisting of hydroxyl, halogen, alkyl, alkoxy, and amino and n is 0, 1, 2, 3, 4, 5, or 6.

In a particular embodiment of a method of producing a non-human animal model of corneal angiogenesis according to the invention, an effective amount of the aromatic compound of formula (I) administered is about 1 µmol to about 70 µmol.

In another general aspect, the invention relates to a method of producing a non-human animal model of a corneal ectatic disease, the method comprising applying to a cornea of at least one eye of a non-human animal an effective amount of an aromatic compound of formula (I):

wherein R is selected from the group consisting of hydroxyl, halogen, alkyl, alkoxy, and amino, and n is 0, 1, 2, 3, 4, 5, or 6.

In a particular embodiment of a method of producing a non-human animal model of a corneal ectatic disease according to the invention, an effective amount of the aromatic compound of formula (I) is about 30 µmol to about 85 µmol.

In yet another general aspect, the invention relates to a method of screening compounds to modulate corneal angiogenesis or a corneal ectatic disease, the method comprising:
(i) preparing a non-human animal model of corneal angiogenesis or a corneal ectatic disease by a method comprising applying to a cornea of at least one eye of a non-human animal an effective amount of an aromatic compound of formula (I):

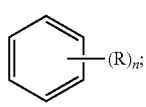

(ii) administering a test compound to the at least one eye of the non-human animal model; and
(iii) determining an effect of the test compound on at least one of blood vessel growth in a cornea and structural distortion of a cornea in the at least one eye,
wherein R is selected from the group consisting of hydroxyl, halogen, alkyl, alkoxy, and amino, and n is 0, 1, 2, 3, 4, 5, or 6.

Other aspects of the invention relate to non-human animal models of corneal angiogenesis and corneal keratoconus produced by the methods of the invention.

In particularly preferred embodiments of the invention, an aromatic compound of formula (I) is benzene or phenol.

In yet another general aspect, the invention relates to a method of identifying substances harmful to human health, the method comprising:
(i) applying a test substance to a cornea of at least one eye of a non-human animal; and
(ii) determining an effect of the test substance on at least one of blood vessel growth in the cornea and structural distortion of the cornea.

The details of one or more embodiments of the invention are set forth in the description below. Other features and advantages will be apparent from the following detailed description, the drawings, and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown in the drawings and described in the following detailed description of the invention. In the drawings:

FIG. 1A: photographic image of the right eye prior to application of phenol; and FIG. 1B: photographic image of the right eye 3 weeks after a single topical application of 3.0 M phenol solution (10 µl), and an inset showing a schematic representation of the observed growth of blood vessels in the cornea; FIG. 1C: image of a section of a corneal epithelium membrane stained with hematoxylin and eosin stain eight weeks after a single topical application of 3.0 M phenol solution (10 µl);

FIG. 2A: eye treated with 4.0 M benzene solution (10 µl); FIG. 2B: eye treated with 6.0 M benzene solution (10 µl); and FIG. 2C: eye treated with 7.0 M benzene solution (10 µl)

DETAILED DESCRIPTION OF THE INVENTION

Figure 1A:
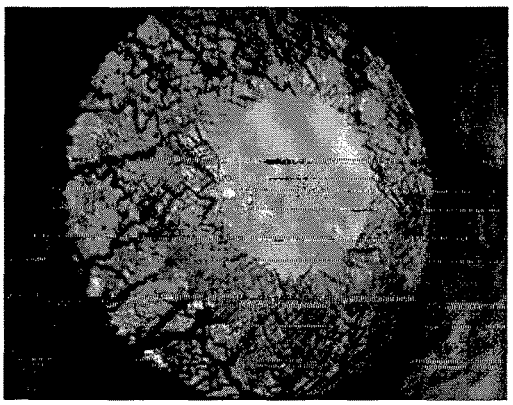
FIGS. 1A, 1B, and 1C show photographic images of the right eye of a Wistar rat before and after treatment with a 3.0 M phenol solution.

All patents and publications referred to herein are incorporated by reference. Unless otherwise defined, all technical and scientific terms used herein have the same meaning as commonly understood by one of ordinary skill in the art to which this invention pertains. Otherwise, certain terms used herein have the meanings as set forth in the specification.

It must be noted that as used herein and in the appended claims, the singular forms "a," "an," and "the" include plural references unless the context clearly dictates otherwise.

As used herein, the term "non-human animal" refers to any animal, most preferably a mammal, which is not a human. Examples of mammals include cows, dogs, cats, horses, pigs, monkey, sheep, and rodents. Examples of rodents include rats, mice, rabbits, and guinea pigs. Preferably, a non-human animal is a rodent selected from the group consisting of rats, mice, rabbits, and guinea pigs, and is more preferably a rat.

The term "cornea," as used herein, refers to the transparent tissue at the front of the eye that covers the iris, pupil, and anterior chamber. The cornea is avascular, meaning that it normally has no blood vessels. The cornea also typically has a rounded shape.

As used herein, "angiogenesis" and "neovascularization" refer to the physiological process by which new blood vessels form from preexisting blood vessels. As used herein, the terms "corneal angiogenesis" and "corneal neovascularization" refer to the growth of one or more new blood vessels in the cornea. Because the cornea is avascular, i.e., does not contain any blood vessels, any new blood vessels in the cornea typically arise from the growth of blood vessels from the limbal vascular plexus area of the eye into the cornea.

As used herein, "fibrosis" refers to the formation of fibrous connective tissue in an organ or tissue, usually as a result of a reparative or regenerative process. The fibrous connective tissue can be scar tissue.

As used herein, "corneal ectasia" and "corneal ectatic disease" refer to a noninflammatory disease of the cornea characterized by irregularities in the cornea that cause disturbances in vision as a result of astigmatism. Corneal ectasia refers to a group of conditions including keratoconus, pellucid marginal degeneration, keratoglobus, and posterior keratoconus, with the most prevalent, particularly in humans, being keratoconus.

According to a preferred embodiment of the invention, a corneal ectatic disease is keratoconus. The term "corneal keratoconus" refers to a disease that affects the structure of the cornea. In corneal keratoconus, the shape of the cornea slowly changes from the typical round shape to a conical shape that bulges outward, forming a protrusion. Corneal keratoconus can also be described as "the loss of shape" of the cornea.

As used herein, "structural distortion," when used with reference to the cornea, means a change in shape of the cornea characterized by a bulging or protruding of the cornea. In a particular embodiment, "structural distortion" refers to a change in shape of the cornea from a rounded shape to a conical shape that protrudes outward from the eye.

As used herein "an effective amount" refers to an amount of a compound of formula (I) needed to induce the desired physiological result. In one embodiment, an effective amount is an amount that induces the growth of one or more new blood vessels in the cornea. In another embodiment, an effective amount is an amount that causes a structural distortion of the cornea.

As used herein, the term "alkyl" means a saturated, unbranched or branched hydrocarbon chain containing at least one carbon atom, preferably 1-20 carbons, and more preferably 1-3 carbon atoms. Examples of unbranched alkyl groups include, but are not limited to, methyl, ethyl, propyl, butyl, pentyl, and hexyl. Examples of branched alkyl groups include, but are not limited to, isopropyl and tert-butyl.

As used herein, the term "alkoxy" denotes a unit having the general formula —OR, wherein R represents an alkyl group. Examples of alkoxy groups include, but are not limited to, methoxy, ethoxy, propoxy, and butoxy.

As used herein, the term "halogen" has its ordinary meaning as would be known to one of ordinary skill in the art. Non-limiting examples of halogens include fluoro, bromo, chloro, and iodo.

An alkyl group can be unsubstituted or substituted with one or more suitable substituents. When an alkyl group is substituted, it can have one or more substituents, preferably from 1 to 3 substituents, and more preferably from 1 to 2 substituents. Representative examples of suitable substituents with which an alkyl group can be substituted include, but are not limited to, halogens, such as fluoro, chloro, bromo, and iodo; hydroxyl; alkoxy, such as methoxy, ethoxy, and propoxy; and amino.

The invention relates to non-human animal models of corneal angiogenesis and corneal ectatic diseases, such as corneal keratoconus. The non-human animal models are produced by applying an aromatic compound, such as benzene or phenol, to an eye of a non-human animal. The inventor surprisingly discovered that depending on the amount of aromatic compound applied to the eye, corneal angiogenesis and/or corneal ectatic diseases can be induced. For example, lower amounts of aromatic compounds induce corneal angiogenesis, whereas increased amounts of aromatic compounds are typically needed to induce corneal ectatic diseases.

In one general aspect, the invention relates to a method of producing a non-human animal model of corneal angiogenesis. According to embodiments of the invention, the method comprises applying to at least one eye of a non-human animal an effective amount of an aromatic compound of formula (I):

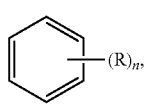

(I)

wherein R is selected from the group consisting of hydroxyl, halogen, alkyl, alkoxy, and amino and n is 0, 1, 2, 3, 4, 5, or 6.

According to preferred embodiments of the invention, the aromatic compound of formula (I) is benzene or phenol. Benzene is an aromatic compound of formula (I), wherein n is 0. Phenol is an aromatic compound of formula (I), wherein R is hydroxyl and n is 1. In a particularly preferred embodiment, the aromatic compound is phenol.

An effective amount of the aromatic compound of formula (I) can be applied to the eye of a non-human animal by any method known in the art including, but not limited to, topical application and injection. Preferably, an effective amount of the aromatic compound of formula (I) is administered topically. Examples of topical compositions that can be used with the invention include, but are not limited to, creams, gels, ointments, and liquid compositions, such as solutions, suspensions, and eye drops. Preferred topical compositions include liquid compositions, and particularly eye drops.

According to embodiments of the invention, a compound of formula (I) can be topically applied to the cornea by any method known in the art in view of the present disclosure. Non-limiting examples of methods for topically applying a compound of formula (I) include by drops and by swabbing. Preferably, the compound of formula (I) is administered to the cornea by drops.

In a preferred embodiment of the invention, an aromatic compound of formula (I) is topically applied to the eye in a liquid composition, and more preferably in the form of an aqueous vehicle. As used herein, an "aqueous vehicle" is a liquid composition comprising water and an aromatic compound of formula (I). Non-limiting examples of aqueous vehicles include solutions, suspensions, eye drops and the like. In a particular embodiment of the invention, an aqueous vehicle contains water and benzene or phenol.

According to embodiments of the invention, the aromatic compound of formula (I) is applied to the cornea of the eye, and is preferably applied directly to the center of the cornea. The aromatic compound of formula (I) can be applied to one eye, or to both eyes of the animal. In certain embodiments of the invention, applying the aromatic compound of formula (I) to only one eye of the animal is preferred, because this allows for the second, untreated eye to serve as a control.

According to embodiments of the invention, an effective amount of a compound of formula (I) needed to produce a non-human animal model of corneal angiogenesis is about 1 μmol to about 70 μmol, and more preferably 30 μmol to 70 μmol, such as about 1 μmol, 5 μmol, 10 μmol, 30 μmol, 40 μmol, 50 μmol, 60 μmol, or 70 μmol. An effective amount of a compound of formula (I) can be applied once, or more than once. Preferably, an effective aromatic compound of formula (I) is administered in a single application.

Because there is a difference in the angiogenic response between different animal species, and sometimes between animals of the same species, the effective amount of an aromatic compound of formula (I) to apply to an eye of the animal to induce corneal angiogenesis can depend on various factors including, but not limited to, the particular species of animal, the age of the animal, etc. One of ordinary skill in the art would readily be able to determine an effective amount of an aromatic compound of formula (I) to be applied to the eye of the non-human animal in order to achieve the desired physiological response in view of the present disclosure. One of ordinary skill in the art will also appreciate that there can be variability between animals of the same species in the angiogenic response to an aromatic compound of formula (I).

Any method known in the art can be used to evaluate the angiogenic activity of any particular amount of an aromatic compound of formula (I) to determine if such amount is effective for inducing the desired amount of corneal angiogenesis. For example, the potency of angiogenic activity can be evaluated by determining the number or growth rate of newly formed capillaries and blood vessels, or by calculating an angiogenic score. An angiogenic score can be calculated according to the following formula: (vessel density)× (distance from the limbus). The limbus is the border of the cornea and the sclera (white of the eye). A vessel density value of 1 corresponds to about 0-25 vessels per cornea; a value of 2 corresponds to about 25-50 vessels per cornea; a value of 3 corresponds to about 50 to 75 vessels per cornea; a value of 4 corresponds to about 75-100 vessels per cornea; and a value of 5 corresponds to more than 100 vessels per cornea. The distance from the limbus can be measured (in mm) with the aid of an ocular grid.

As another illustrative example, angiogenic activity can be evaluated by histological studies. For examples, hematoxylin and eosin (H&E) stains can be used to stain dissected corneal tissue, and detect the formation of new blood vessels. As shown in FIG. 1C, which is an image of a section of a corneal epithelium membrane stained with H&E stain eight weeks after a single topical application of a 3.0 M phenol solution, different biological structures can be detected to assess angiogenic activity and the progression of corneal angiogenesis. In particular, arrow 1 points to normal corneal epithelium, arrow 2 points to new blood vessels growth induced by the application of phenol that would not normally be present in the cornea, and arrow 3 points to the normal stromal tissue of the cornea.

As an illustrative and non-limiting example, when the aromatic compound of formula (I) is benzene or phenol, an effective amount can range from about 1 μmol to about 70 μmol (i.e., about 75 μg to about 5.5 mg), and is preferably from 30 μmol to 70 μmol, such as 1 μmol, 5 μmol, 10 μmol, 30 μmol, 40 μmol, 50 μmol, 60 μmol or 70 μmol.

In a particular embodiment, the non-human animal used in a method of the invention is an albino animal. As used herein, an "albino animal" refers to an animal lacking pigment, and particularly melanin, in at least the eyes. Albino animals produce purer animal models of corneal angiogenesis as compared to pigmented animals, which have melanin in their eyes, because pigmented animals tend to have a greater degree of corneal fibrosis upon application of aromatic compounds of formula (I), and particularly benzene, to the cornea to induce angiogenesis.

The invention also relates to a non-human animal model of corneal angiogenesis produced by a method of the invention. According to embodiments of the invention, non-human animal models of corneal angiogenesis have substantially no fibrosis in the cornea of the eye. Additionally, the non-human animal models of corneal angiogenesis comprise one or more new blood vessels in the cornea of at least one eye of the animal. Because fibrosis is a natural biological process that can occur in tissue repair, some fibrosis can be observed in the cornea of non-human animal models of the invention. However, the amount of fibrosis observed, if any, is significantly less than the amount of fibrosis that is observed with other animal models of corneal angiogenesis.

Non-human animal models of corneal angiogenesis thus have several advantages as compared to prior art animal models of corneal angiogenesis. In particular, due to the substantial absence of fibrosis in the cornea, a purer animal model of corneal angiogenesis is produced. More specifically, prior art animal models of corneal angiogenesis have a complicated angiogenic response, and in addition to the growth of new blood vessels, fibrosis or scar tissue formation is usually also observed in the cornea. The presence of fibrosis and scar tissue makes it difficult and more complicated to understand the angiogenesis process. In contrast, the substantial elimination, or at least significant reduction in the amount of fibrosis observed with the non-human animal models of corneal angiogenesis of the invention allows the angiogenesis process to be more easily studied.

Moreover, less fibrosis and scar tissue formation is observed when phenol is used as compared to the amount observed when benzene is used. Thus, phenol is the preferred aromatic compound of formula (I) for use with the present invention.

In addition to a substantially reduced amount of fibrosis in the cornea, the non-human animal models of corneal angiogenesis according to the invention have other advantages over prior art animal models. For example, the animal models can be produced by simply administering eye drops of a solution of an aromatic compound of formula (I), such as benzene or phenol, to the eye of the non-human animal. Accordingly, surgical procedures are not required. This eliminates many of the complications that are often associated with or result from surgical procedures, such as inflammatory reactions due to tissue manipulation, infection at incision sites, and puncturing of the anterior chamber of the eye. Moreover, suturing is not required, which further reduces complications. Thus, the methods of producing non-human animal models of the invention are simpler to execute, less expensive, and require less time than previous methods for generating animal models of corneal angiogenesis, such as the corneal pocket model.

In another general aspect, the invention relates to a method of producing a non-human animal model of a corneal ectatic disease. According to embodiments of the invention, the method comprises applying to a cornea of at least one eye of a non-human animal an effective amount of an aromatic compound of formula (I):

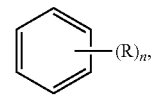

wherein R is selected from the group consisting of hydroxyl, halogen, alkyl, alkoxy, and amino and n is 0, 1, 2, 3, 4, 5, or 6.

Any of the aromatic compounds of formula (I) described herein can be used in a method of producing a non-human animal model of a corneal ectatic disease. In preferred embodiments, the aromatic compound of formula (I) is benzene or phenol.

Any of the methods for applying an aromatic compound of formula (I) to a cornea of an eye of a non-human animal described herein with reference to producing a non-human animal model of corneal angiogenesis according to the invention can be used in a method of producing a non-human animal model of a corneal ectatic disease according to the invention. Preferred methods of application include topical application, and preferred topical compositions include liquid compositions, such as aqueous solutions or other aqueous vehicle. In a preferred embodiment, an aqueous solution or vehicle is applied to the cornea by eye drops.

According to embodiments of the invention, an effective amount of a compound of formula (I) needed to produce a non-human animal model of a corneal ectatic disease is about 30 µmol to 85 µmol, such as 30 µmol, 40 µmol, 50 µmol, 60 µmol, 65 µmol 70 µmol, 75 µmol, 80 µmol, or 85 µmol. In general, an effective amount of an aromatic compound of formula (I) for producing a non-human animal model of a corneal ectatic disease is greater than an effective amount of an aromatic compound of formula (I) for producing a non-human animal model of corneal angiogenesis. The effective amount can be applied in a single application or in multiple applications, and is preferably applied in a single application.

In a particular embodiment of the invention, about 70 µmol to 85 µmol of benzene (i.e., about 5.5 mg to about 7.0 mg benzene) can be applied to the eye of a non-human animal to produce a model of corneal keratoconus. For example, applying a 7.0 M to 8.5 M benzene in an aqueous vehicle such as in the form of eye drops can induce a structural distortion of the cornea, resulting in a model of corneal keratoconus. See FIG. 3. In another particular embodiment, about 30 µmol to 85 µmol of phenol can be applied to the eye of a non-human animal to produce a model of corneal keratoconus.

In a preferred embodiment of the invention, the corneal ectatic disease is corneal keratoconus. Corneal keratoconus is one of the more common corneal ectatic diseases that develops in humans. According to embodiments of the invention, in a non-human animal model of corneal keratoconus, the structural distortion of the cornea can be characterized as a change in shape from a rounded shape of the cornea to a conical shape. See, e.g., FIG. 3. As corneal keratoconus develops following application of an aromatic compound of formula (I), the cornea begins to thin and protrude outward from the eye, creating a bulge.

According to particular embodiments, an albino animal can be used in a method of the invention for producing a non-human animal model of a corneal ectatic disease.

The invention also relates to non-human animal models of corneal ectatic diseases produced by a method of the invention. According to embodiments of the invention, a non-human animal model of a corneal ectatic disease has a cornea comprising a structural distortion characterized as a change in shape form a rounded shape to a conical shape.

To the best of the knowledge of the inventor, until now there was no known animal model of corneal ectatic diseases, such as corneal keratoconus. The invention thus satisfies this need by providing an animal model of corneal ectatic diseases that is simple and inexpensive to produce, and also does not require complicated equipment.

According to embodiments of the invention, a smaller amount of an aromatic compound of formula (I) is needed to induce corneal angiogenesis as compared to the amount needed to induce a corneal ectatic disease in a method of producing a non-human animal model, as described herein. For example, about 1 µmol to 70 µmol of benzene or phenol are sufficient for inducing corneal angiogenesis when applied to the eye of a non-human animal, whereas about 70 µmol to 85 µmol of benzene, or 30 µmol to 70 µmol of phenol, are needed to induce a corneal ectatic disease, such as corneal keratoconus. See, e.g., FIG. 2 and FIG. 3.

Therefore, as an illustrative example, in a method of producing a non-human animal model of corneal angiogenesis, 10 µL of a 0.1 M to 7.0 M benzene solution can be administered to an eye of a non-human animal, whereas in a method of producing a non-human animal model of a corneal ectatic disease, 10 µL of a 7.0 M to 8.5 M benzene solution can be administered to an eye of a non-human animal. The concentration of benzene can also be varied to adjust the rate at which corneal angiogenesis is induced, and to adjust the amount of new blood vessel growth. See FIG. 2, which demonstrates that the amount of blood vessel growth observed in rat corneas increases as the concentration of benzene applied increases. Of course, one of ordinary skill in the art will readily appreciate that there can be biological variability between species of the same animal in both the angiogenic response and development of corneal keratoconus or other corneal ectatic diseases observed.

Because corneal angiogenesis can be induced by a smaller amount of an aromatic compound of formula (I) than the amount needed to induce corneal ectatic diseases, animal models of corneal ectatic diseases can also comprise one or more new blood vessels in the cornea of the eye as well as the structural distortions of the cornea observed upon application of high concentrations of an aromatic compound of formula (I). This is because when higher concentrations of the aromatic compounds of formula (I) are used, new blood vessels typically grow in addition to causing a structural distortion of the cornea.

According to embodiments of the invention, an anesthetic agent can be administered to the eye of a non-human animal in addition to an aromatic compound of formula (I) in a method of producing a non-human animal model of corneal angiogenesis or a corneal ectatic disease. An anesthetic agent is a drug that causes an analgesic effect, i.e., induces the absence of pain and/or sensation. Any anesthetic agent used in surgical eye procedures can be used, including topical, local, and general anesthetic agents. Preferably, a local anesthetic agent is used. Examples of anesthetic agents that can be used with the invention include, but are not limited to, xylocaine, paracaine, tetracaine, bupivacaine, and lidocaine. The anesthetic agent can be administered by any method known in the art for administering anesthetic agents for surgical eye procedures, such as by topical application. The anesthetic agent can also be administered to the eye in the same composition as the aromatic compound of formula (I), e.g., aqueous solution.

A purpose of administering an anesthetic agent is to reduce any pain or discomfort associated with application of the aromatic compound of formula (I). The anesthetic agent can be administered to the eye before the aromatic compound of formula (I), simultaneously with the application of the aromatic compound of formula (I), or after the aromatic compound of formula (I) is applied, and is preferably applied before or simultaneously with application of the aromatic compound of formula (I).

In other general aspects, the invention relates to methods of studying corneal angiogenesis and corneal ectatic diseases (e.g., keratoconus) using non-human animal models of the invention. For example, the non-human animal models of the invention can be used to screen compounds that modulate corneal angiogenesis to identify modulators of corneal angiogenesis that can be used to treat or prevent diseases associated with increased or decreased in vivo angiogenesis. The non-human animal models of the invention can also be used to screen compounds that are effective in treating or preventing corneal ectatic diseases, such as corneal keratoconus.

According to embodiments of the invention, a method of screening compounds to modulate corneal angiogenesis or a corneal ectatic disease comprises:

(i) preparing a non-human animal model of corneal angiogenesis or of a corneal ectatic disease comprising applying to at least one eye of a non-human animal an effective amount of an aromatic compound of formula (I);
(ii) administering a test compound to the at least one eye of the non-human animal model; and
(iii) determining an effect of the test compound on at least one of blood vessel growth in a cornea and structural distortion of a cornea.

Any of the methods described herein can be used to produce a non-human animal model for use in a method of screening a compound according to the invention.

According to embodiments of the invention, a test compound can be administered prior to, at the same time as, or after application of the aromatic compound of formula (I). A test compound can be administered by any method known in the art, including, but not limited to topical application and injection. Preferably, test compounds are administered topically, such as in a liquid composition, solution, or aqueous vehicle. In certain embodiments, a test compound and an effective amount of an aromatic compound of formula (I) are administered together in a single composition. The test compound and the effective amount of an aromatic compound of formula (I) can be administered to one eye of the non-human animal, and the effective amount of the aromatic compound of formula (I) can be administered to the other eye. By comparing the eye treated with the test compound to the eye not treated with the test compound, the effects of the test compound on corneal angiogenesis and/or corneal ectatic diseases can be determined.

As used herein, the term "modulate" means having an effect on the onset, occurrence of, or progression of corneal angiogenesis or a corneal ectatic disease. In one embodiment, modulate refers to inhibiting the onset of, slowing the progression of, or ameliorating one or more signs or symptoms of corneal angiogenesis or a corneal ectatic disease. In one particular embodiment, modulate refers to increasing or decreasing corneal angiogenesis, e.g. the growth of new blood vessels. In another particular embodiment, modulate refers to reducing or inhibiting the development of structural distortion, or "loss of shape" of the cornea.

According to embodiments of the invention, modulators of corneal angiogenesis can be useful for treating or preventing corneal angiogenesis by, for example, reducing or eliminating the growth of one or more new blood vessels, and can also be useful in treating or preventing other diseases associated with in vivo angiogenesis. Modulators of corneal ectatic diseases can be useful for treating or preventing corneal ectatic diseases, such as corneal keratoconus.

According to embodiments of the invention, when a test compound is applied to the eye prior to or subsequent to application of the aromatic compound of formula (I), the time between applications can vary from a few minutes, to a few hours, to a few days, depending on the particular test compound, its mode of action, its efficacy, etc. For example, a test compound can be applied to one eye, and then an aromatic compound of formula (I) can be applied to both eyes 24 hours later. As another example, an aromatic compound of formula (I) can be applied to both eyes, and then a test compound can be applied three weeks later after the onset of corneal angiogenesis is observed. One of ordinary skill in the art will be able to appropriately design a screening experiment depending on the desired objective.

According to embodiments of the invention, the effect of a test compound on modulating corneal angiogenesis and/or corneal keratoconus can be determined by any method known in the art in view of the present disclosure. For example, the effect can be determined by visual observation or histological studies. Histological studies can be performed by treating a section of a cornea with a dye that stains blood vessels, and observing under a microscope. An exemplary dye that can be used for histological studies is hematoxylin and eosin stain.

The invention also relates to a method of identifying substances harmful to human health. According to embodiments of the invention, the method comprises:
(i) applying a test substance to a cornea of at least one eye of a non-human animal; and
(ii) determining an effect of the test substance on at least one of blood vessel growth in the cornea and structural distortion of the cornea.

Compounds or materials that induce corneal angiogenesis or corneal ectatic diseases, such as corneal keratoconus, can be harmful to human health. A substance that is "harmful to human health" is one that is toxic, increases the incidence of fatal diseases (e.g., cancer), or produces some other adverse biological reaction, such as irritation, rash, etc. Therefore, by screening a substance for its effect on corneal angiogenesis and corneal ectatic diseases according to a method of the invention, a substance that is harmful to health or that poses significant health risks to mammals, such as humans, can be identified.

According to embodiments of the invention, a method of identifying substances harmful to human health can be used to screen substances used in any industry including, but not limited to, the food industry, the pharmaceutical industry, and the electronics industry. Any substance can be screened, such as a compound, material, solvent, etc. According to embodiments of the invention, the test substance is applied to a cornea of an eye of a non-human animal using any method known in the art in view of the present disclosure, including injection or topical application, such as by drops or by swabbing.

Without wishing to be bound by any theories, one possible explanation for the observed effect of aromatic compounds of formula (I), such as benzene and phenol, on blood vessel growth is summarized as follows. The intrinsic ability of melanin, and its derivatives, analogs, and variants, to split the water molecule into hydrogen and oxygen upon absorption of electromagnetic energy, such as light energy, has previously been reported in U.S. Pat. No. 8,455,145. It is also known that high levels of oxygen have an anti-angiogenic effect. It is believed that benzene and phenol can impair the function of melanocytes, which are the cells that produce melanin. Melanocytes are located, among other places, in the middle layer of the eye. By impairing the function of melanocytes, the amount of melanin produced is significantly reduced, and thus the amount of oxygen produced by melanin is also reduced, decreasing oxygen levels and promoting angiogenesis. On the other hand, it is believed that when melanin is more abundant, the dissociation of water molecules occurs more rapidly and/or more readily, resulting in a higher partial pressure of oxygen, consequently reducing the amount of angiogenesis. Accordingly, it is believed that reduced levels of melanin stimulate angiogenesis, and increased levels of melanin inhibit, or at least significantly decrease, angiogenesis.

Again without wishing to be bound by any theories, it is hypothesized that a smaller amount of a compound of formula (I) is needed to induce corneal angiogenesis than corneal ectatic diseases, because a greater inhibition of melanin production is needed to induce the onset of corneal ectatic diseases. In contrast, less inhibition of melanin production is believed to be sufficient to cause corneal angiogenesis. This hypothesis is based on the observation that corneal angiogenesis can be induced with lower concentrations of aromatic compounds of formula (I), as compared to the concentrations of aromatic compounds of formula (I) needed to induce corneal keratoconus as discussed in more detail in the examples below.

This invention will be better understood by reference to the non-limiting examples that follow, but those skilled in the art will readily appreciate that the examples are only illustrative of the invention and are not to be construed as limiting the invention in any way.

EXAMPLES

Example 1

Rat Model of Corneal Angiogenesis and Corneal Ectatic Disease Produced with Phenol Rat models of corneal angiogenesis and corneal keratoconus were produced as follows. Aqueous solutions of phenol having a concentration of 0.1 M, 0.5 M, 1.0 M, 3.0 M, 5.6 M, or 8.5 M were prepared by mixing phenol and water. The solutions were then sterilized by heating to 100° C. for 15 minutes. Then, 10 µL of the sterile phenol solution was topically applied to the center of the cornea of the right eye of a Wistar rat that was two months old. Five rats were treated for each concentration of phenol tested. The phenol solution was allowed to absorb into the eye, and was applied only once. Because the eye has its own natural protective mechanisms, it was not necessary to wash the eye at the end of the application.

Figure 1B:
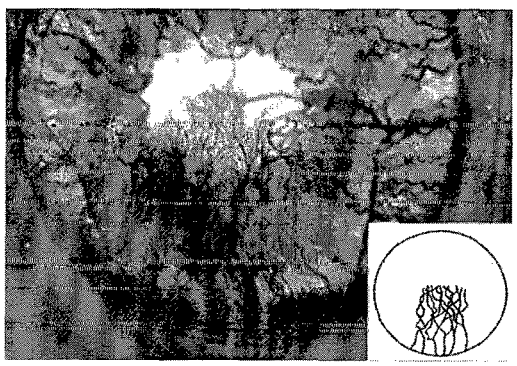
Figure 1C:
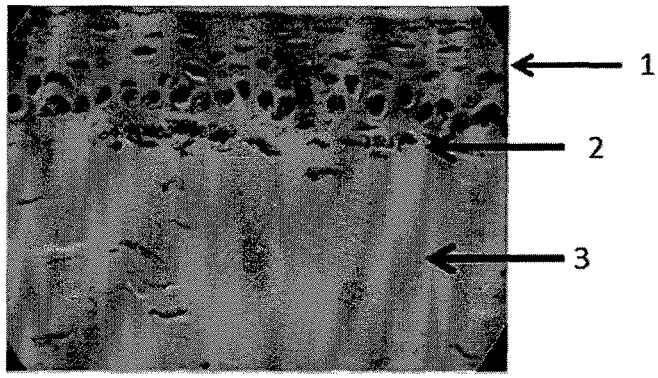

Prior to application of the phenol solution, there were no visible blood vessels in the cornea (FIG. 1A). Instead, the vessels seen are in the iris of the eye. However, new blood vessels began to form in the cornea upon treatment with all concentrations of the phenol solution tested in at least one of the rats in each group one week after application of the aqueous phenol solution. The amount of new blood vessels observed in the cornea was even greater three weeks after application (FIG. 1B, application of 3 M solution). Blood vessel growth was observed for a period of fourth months. As shown in FIG. 1B, profuse vascularization began in the sclero-corneal limbus and progressed towards the center of the corneal surface. Except for the new corneal vessels, no other anatomical or inflammatory alterations were observed. The vessels of the iris were deeper than those that grew in the cornea, and are delimited by the pupil border. At the higher concentrations of phenol tested (3.0 M, 5.6 M, and 8.5 M), changes associated with corneal ectasia, particularly corneal keratoconus, were also observed in some of the rats. The results are summarized in Table 1 below.

TABLE 1

Preparing rat models of corneal angiogenesis and corneal keratoconus with phenol in rats.

| Phenol Concentration | Number of Rats Treated | Observation in Treated Eye (Number of Rats) | | |
|---|---|---|---|---|
| | | Angiogenesis | Corneal Keratoconus | No Change |
| 0.1M | 5 | 1 | 0 | 4 |
| 0.5M | 5 | 1 | 0 | 4 |
| 1.0M | 5 | 3 | 0 | 2 |
| 3.0M | 5 | 4 | 2 | 1 |
| 6.5M | 5 | 4 | 2 | 1 |
| 8.5M | 5 | 3 | 1 | 2 |

Histological studies were performed after eight weeks following the application of phenol. The cornea was excised, and a piece of the corneal epithelium was stained with hematoxylin and eosin stain. As shown in FIG. 1C, well differentiated blood vessels can be seen under the basal membrane of the corneal epithelium (pointed to by arrow 2).

The results of the experiment shown above in Table 1 demonstrate that phenol applied directly to the eye of a rat induces corneal angiogenesis, and that animal models of corneal angiogenesis can be produced by applying phenol to an eye of the animal. The results also indicate that when higher concentrations of phenol are applied, corneal ectatic diseases are also induced.

Example 2

Rat Model of Corneal Angiogenesis Produced with Benzene

Rat models of corneal angiogenesis were produced as follows. Aqueous benzene compositions having the desired concentration (between 3.0 M and 7.0 M) were prepared by mixing benzene and water. The aqueous composition was then sterilized by heating to 100° C. for 15 minutes. In particular, 3.0 M, 4.0 M, 5.0 M, 6.0 M, or 7.0 M aqueous benzene compositions were prepared. Then, 10 µL of each composition was topically applied to the center of the cornea of the right eye of a Wistar rat that was two to three months old. The benzene aqueous composition was allowed to absorb into the eye, and was applied only once. Because the eye has its own natural protective mechanisms, it was not necessary to wash the eye at the end of the application.

Figure 2A:
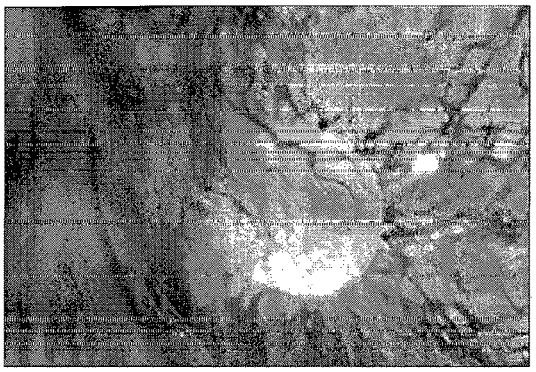
FIGS. 2A, 2B, and 2C show photographic images of the right eye of Wistar rats treated with a single application of benzene solution of varying concentrations 15 days after application of the benzene solution.
Figure 2B:
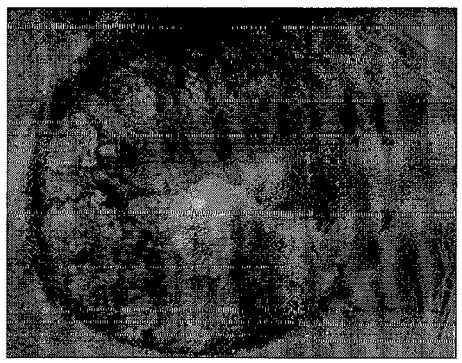
Figure 2C:
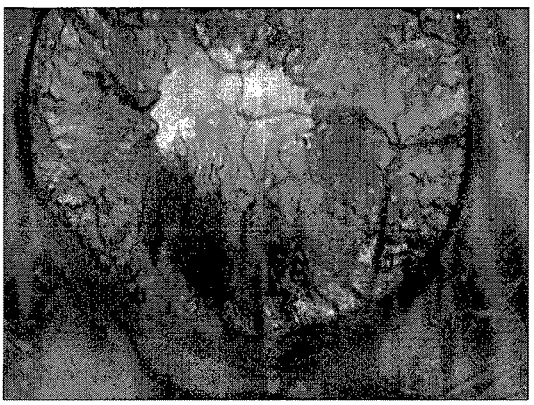

Prior to benzene application, there were no visible blood vessels in the cornea, and the corneas of the rats appeared similar to that as shown in FIG. 1A. However, as shown in FIG. 2, new blood vessels began to form in the cornea upon treatment with all concentrations of benzene as early as 15 days after application. The amount of new blood vessels observed in the cornea was even greater three weeks after application, and the observed growth of new blood vessels persisted for at least four months from the initial application of benzene, at which time the eyes were sacrificed for histological studies.

The results of the experiment demonstrate that benzene applied directly to the eye of a rat induces corneal angiogenesis, and that animal models of corneal angiogenesis can be produced by applying benzene to an eye of the animal. The results also indicate that when higher concentrations of benzene were initially applied, the amount of new blood vessels observed within 15 days of application also increased. Thus, the amount of new blood vessel growth in rats can depend upon the concentration of the aromatic compound, with higher concentrations able to more rapidly induce corneal angiogenesis as compared to lower concentrations. The results further indicate that the amount of corneal angiogenesis observed increases over time following the initial application of the aromatic compound.

Example 3

Rat Model of Corneal Keratoconus

A rat model of corneal keratoconus was produced as follows. An aqueous benzene composition having a concentration of 7.0 M to 8.5 M was prepared by mixing water and benzene. The composition was then sterilized by heating the solution to 100° C. for 15 minutes. The aqueous benzene composition (10 µL) was topically applied directly to the center of the cornea of one eye of a Wistar rat by micropipetting. The rat was three months old, and benzene was applied only once.

Figure 3:
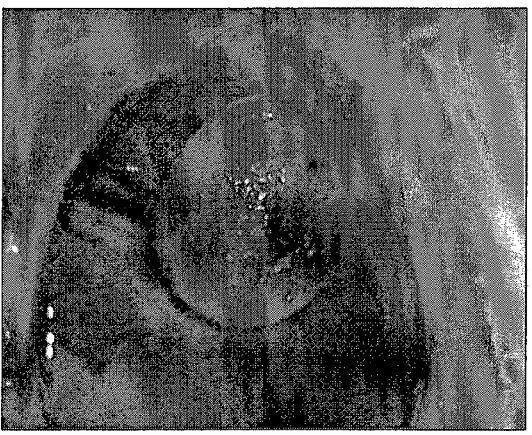
FIG. 3 shows a photographic image of an eye of a Wistar rat 15 days after application of a 7.0 M aqueous benzene solution.

In addition to angiogenesis (i.e., new blood vessel growth), the corneal tissue was characterized by marked thinning, and outward protrusion (FIG. 3). The observed changes in the cornea, which began to occur within the first week following benzene application, started as changes in corneal transparency, followed by the growth of new blood vessels in the periphery of the cornea (i.e., angiogenesis), and finally protrusion of the cornea within the second week following application. The changes were compatible with non-inflammatory corneal ectasia, and particularly corneal keratoconus.

It should also be noted that when 10 µL of a 9.0 M aqueous benzene composition were applied to the eyes of Wistar rats according to the same procedure, corneal keratoconus was so severe that the rats developed endophthalmitis (intraocular infection).

The results of the experiment indicate that applying benzene to the eye of rats induces corneal keratoconus, and that animal models of corneal keratoconus can be produced by administering aromatic compounds of formula (I) to an eye of the animal.

Example 4

Screening Compounds that Modulate Corneal Angiogenesis and/or Corneal Ectatic Diseases Potential therapeutic agents (i.e., test compounds) are tested for modulation of corneal angiogenesis and corneal ectatic diseases. An aqueous solution of an aromatic compound of formula (I) is prepared, and topically applied in the form of eye drops to the cornea of both eyes of a rodent. Then, a solution of a candidate therapeutic agent is topically applied to the cornea of one eye of the rodent. The eyes of the rodent are observed, and the eye treated with the candidate therapeutic agent is compared to the untreated eye to determine the efficacy of the test compound, if any, in modulating corneal angiogenesis or a corneal ectatic disease. Visual observation and histological studies are performed to determine the effects of the test compound.

Example 5

Identifying Substances Harmful to Human Health

Potentially harmful substances and materials (i.e., test substances) are tested for their effect on inducing corneal angiogenesis and corneal ectatic diseases. The test substance is topically applied to a cornea of one eye of the rodent. The eyes of the rodent are observed, and the eye treated with the test substance is compared to the untreated eye to determine the effect of the test substance, if any, in causing corneal angiogenesis or a corneal ectatic disease. Visual observation and histological studies are performed to determine the effects of the test substance. Test substances that induce corneal angiogenesis or corneal ectatic diseases are identified as potentially harmful to human health.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claim.

I claim:

1. A method of producing a non-human animal model of corneal angiogenesis, the method comprising applying to a cornea of at least one eye of a non-human animal an effective amount of an aromatic compound selected from the group consisting of phenol and benzene, wherein the effective amount of the aromatic compound applied is about 1 µmol to about 70 µmol, and the effective amount of the aromatic compound is applied as a composition having a concentration of 0.1 M to 8.5 M.

2. The method of claim 1, wherein the aromatic compound is phenol.

3. The method of claim 1, wherein the non-human animal is a rodent.

4. The method of claim 1, further comprising administering an anesthetic agent to the at least one eye.

5. A non-human animal model of corneal angiogenesis prepared by the method of claim 1, wherein the non-human animal model has substantially no fibrosis in the cornea.

6. A method of screening compounds to modulate corneal angiogenesis, the method comprising:
 (i) preparing a non-human animal model of corneal angiogenesis by a method comprising applying to a cornea of at least one eye of a non-human animal an effective amount of an aromatic compound selected from the group consisting of benzene and phenol, wherein the effective amount of the aromatic compound applied is about 1 µmol to about 70 µmol, and the effective amount of the aromatic compound is applied as a composition having a concentration of 0.1 M to 8.5 M;
 (ii) administering a test compound to the at least one eye of the non-human animal model; and
 (iii) determining an effect of the test compound on blood vessel growth in the cornea.

7. The method of claim 6, wherein the test compound is administered to the at least one eye prior to, simultaneously with, or after application of the aromatic compound.

8. The method of claim 6, wherein the aromatic compound is phenol.

9. The method of claim 2, wherein the effective amount of phenol applied is about 1 µmol to about 10 µmol.

10. The method of claim 1, wherein the aromatic compound is benzene.

11. The method of claim 10, wherein the effective amount of benzene applied is about 30 µmol to about 70 µmol.

12. The method of claim 8, wherein the effective amount of phenol applied is about 1 µmol to about 10 µmol.

13. The method of claim 6, wherein the aromatic compound is benzene.

14. The method of claim 13, wherein the effective amount of benzene applied is about 30 µmol to about 70 µmol.

15. The method of claim 1, wherein the effective amount of the aromatic compound is applied as an aqueous vehicle.

16. The method of claim 2, wherein the effective amount of phenol is applied as an aqueous vehicle.

17. The method of claim 10, wherein the effective amount of benzene is applied as an aqueous vehicle.

18. The method of claim 6, wherein the effective amount of the aromatic compound is applied as an aqueous vehicle.

19. The method of claim 8, wherein the effective amount of phenol is applied as an aqueous solution.

20. The method of claim 13, wherein the effective amount of benzene is applied as an aqueous solution.

\* \* \* \* \*